United States Patent [19]

Mouzin et al.

[11] 4,372,975
[45] Feb. 8, 1983

[54] SUBSTITUTED 2-BENZOYL-4-CHLOROGLYCINANILIDE DERIVATIVES, A PROCESS FOR THEIR PRODUCTION, AND THEIR USE AS MEDICAMENTS

[75] Inventors: Gilbert Mouzin; Henri Cousse; Antoine Stenger, all of Castres, France; Sylvano Casadio, Milan, Italy

[73] Assignee: Pierre Fabre SA, Paris, France

[21] Appl. No.: 200,622

[22] Filed: Oct. 27, 1980

Related U.S. Application Data

[63] Continuation-in-part of Ser. No. 916,651, Jun. 19, 1978, abandoned.

[30] Foreign Application Priority Data

Jun. 16, 1977 [FR] France ............................... 77 18511

[51] Int. Cl.³ ................ A61K 31/165; C07C 103/133
[52] U.S. Cl. .................... 424/324; 424/248.54; 424/250; 424/267; 424/273 R; 544/159; 544/397; 546/232; 546/233; 546/234; 548/341; 564/164; 564/168; 564/190; 564/195
[58] Field of Search ............... 564/164, 168, 195, 190; 424/324, 267, 248.54, 250, 273 R; 546/232, 233, 234; 544/159, 397; 548/341

[56] References Cited

U.S. PATENT DOCUMENTS

| | | | |
|---|---|---|---|
| 3,202,699 | 8/1965 | Stempel | 564/195 |
| 3,914,215 | 10/1975 | Tachikawa et al. | 564/164 |
| 3,927,010 | 12/1975 | Hellerbach et al. | 564/195 |
| 4,075,409 | 2/1978 | Greve et al. | 564/195 |

FOREIGN PATENT DOCUMENTS

471999 1/1974 Australia .
50-148340 11/1975 Japan .

OTHER PUBLICATIONS

Meyer, et al., Pharmazie, 1972, 27 (1), pp. 32–42.

*Primary Examiner*—Arthur P. Demers
*Attorney, Agent, or Firm*—Alan H. Levine

[57] ABSTRACT

The invention relates to new substituted 2-benzoyl-4-chloroglycinanilide derivatives, to a process for their production and to their use as medicaments.

The new derivatives according to the invention correspond to the general formula

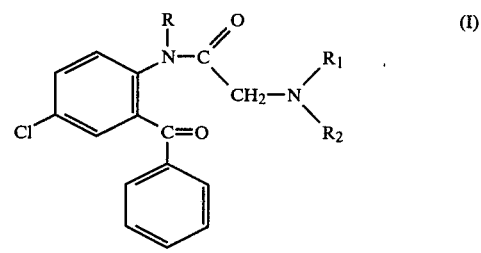

in which:

R may be a linear or branched alkyl group, preferably a lower alkyl group;

$R_1$ and $R_2$ may be the same or different and are selected from hydrogen, alkyl, alkenyl, alkynyl, hydroxy alkyl, alkoxy alkyl and aralkyl groups, these various groups optionally being linear or branched, and from 3- to 6-membered cycloalkyl groups optionally substituted on the α-carbon atom by an alkynyl radical;

in addition, the groups $R_1$ and $R_2$ may form with the nitrogen atom to which they are attached an optionally saturated 5-membered or 6-membered nitrogen heterocycle optionally containing a second heteroatom selected from oxygen and nitrogen, said heterocycle optionally being substituted, preferably on the second nitrogen atom, by a lower alkyl radical; and their salts obtained with therapeutically acceptable mineral or organic acids.

17 Claims, No Drawings

SUBSTITUTED 2-BENZOYL-4-CHLOROGLYCINANILIDE DERIVATIVES, A PROCESS FOR THEIR PRODUCTION, AND THEIR USE AS MEDICAMENTS

This application is a continuation-in-part of copending application Ser. No. 916,651, filed June 19, 1978, now abandoned.

This invention, developed at the Centre de Recherches PIERRE FABRE, relates to new substituted 2-benzoyl-4-chloroglycinanilide derivatives, to a process for their production and to their use as medicaments.

The new derivatives according to the invention correspond to the general formula:

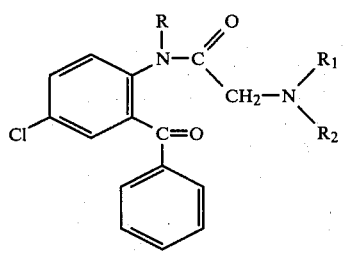

in which
R represents a linear or branched alkyl group, preferably a lower alkyl group;
$R_1$ and $R_2$ may be the same or different and are selected from hydrogen, alkyl, alkenyl, alkynyl, hydroxy alkyl, alkoxy alkyl and aralkyl groups, these various groups optionally being linear or branched, and from 3- to 6-membered cycloalkyl groups optionally substituted on the α-carbon atom by an alkynyl radical;
in addition, the groups $R_1$ and $R_2$ may form with the nitrogen atom to which they are attached an optionally saturated 5-membered or 6-membered nitrogen heterocycle optionally containing a second heteroatom selected from oxygen and nitrogen, said heterocycle optionally being substituted, preferably on the second nitrogen atom, by a lower alkyl radical.

Some of the meanings given to the radicals R, $R_1$ and $R_2$ are illustrated in the following. The alkyl groups are straight-chain or branched-chain alkyl groups, such as methyl, ethyl, propyl, isopropyl, butyl, isobutyl, sec.-butyl, tert.-butyl, pentyl, isopentyl, neopentyl, tert.-pentyl, hexyl, isohexyl, heptyl, etc. The alkoxy substituents may be selected for example from the methoxy, ethoxy, propoxy, isopropoxy groups, etc. The aralkyl groups may be selected from the benzyl, phenethyl, phenyl propyl groups, etc. The alkenyl groups may be selected from the allyl, butenyl, pentadienyl groups, etc. The alkenyl groups may be selected from the ethinyl, propargyl groups, etc. Finally, the optionally saturated heterocycles are selected for example from the pyrrolyl, imidazolyl, pyrazolyl, isoxazolyl, pyridyl, pyrazinyl, pyrinidinyl, pyridazinyl, pyrrolidinyl, imidazolidinyl, pyrazolidinyl, piperidyl, piperazinyl, morpholinyl groups, etc.

The present invention also relates to salts of the compounds of formula I obtained with therapeutically acceptable acids. Examples of therapeutically or physiologically acceptable addition salts are the salts of mineral acids, such as hydrochloric acid, phosphoric acid and sulphuric acid, and the salts of organic acids, such as succinic acid, tartaric acid, etc.

The invention also relates to a process for the production of compounds corresponding to formula I, comprising reacting a compound corresponding to the general formula

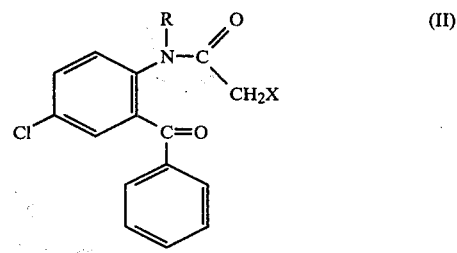

in which:
R has the same meaning as in general formula I and
X represents a halogen atom,
with an amine corresponding to the general formula

in which: $R_1$ and $R_2$ have the same meaning as in general formula I.

The starting products of general formula II may be prepared in accordance with one of the following reaction schemes:

(a) Tosylate process

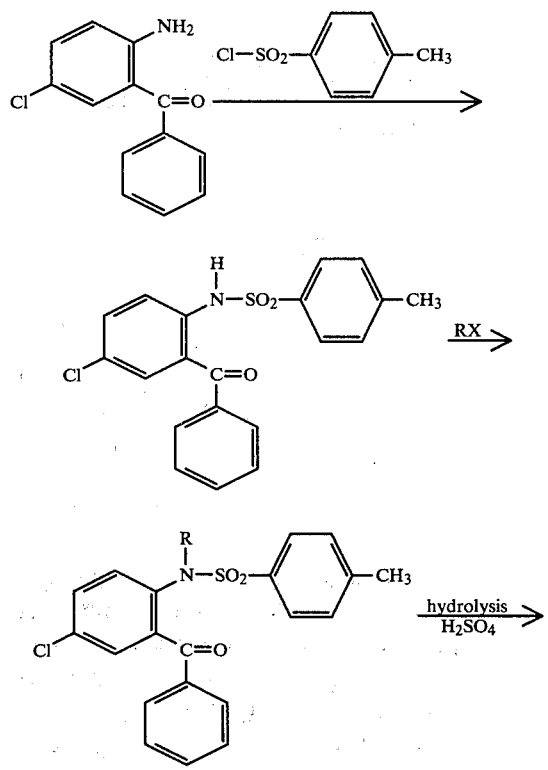

-continued

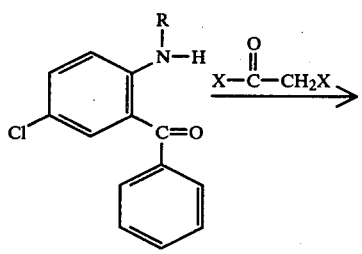

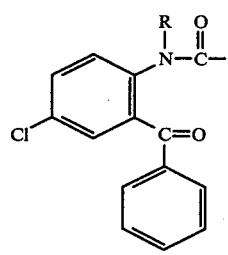

X and R being as defined above.

(b) Alkyl sulphate process

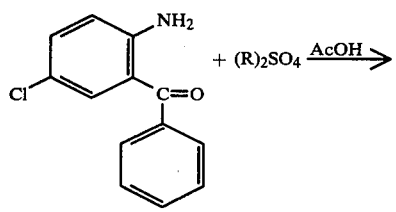

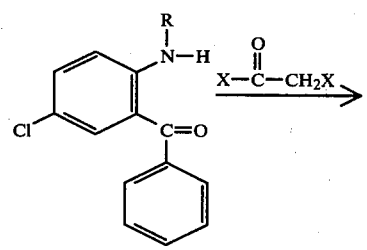

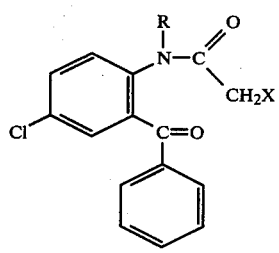

Finally, the invention relates to the use of the compounds of general formula I as medicaments showing activity on the central nervous system and, in particular, as anxiolytic agents, sedatives, anticonvulsive agents, hypnotic agents or as muscle relaxants.

The invention is described in more detail in the following Examples:

EXAMPLE 1

N-Isopropyl-N'-methyl-(2-benzoyl-4-chloro)-glycinanilide hydrochloride (a) Production of 2-tosylamido-5-chlorobenzophenone 190.6 g of tosyl chloride are added to a solution of 208.5 g (0.9 mole) of 2-amino-5-chlorobenzophenone in 500 cc of pyridine at such a rate that the temperature of the reaction medium does not exceed 48° C. After this addition, stirring is continued for 15 minutes, after which the temperature is increased for 1 hour to 100° C.

A homogeneous brown-coloured solution is thus obtained. After the reaction medium has returned to ambient temperature, it is hydrolysed by pouring into 4 liters of 3 N hydrochloric acid in the presence of ice, resulting in the formation of a thick oil which crystallises.

The crystals are recovered by filtration and are dissolved in 2 liters of ethylacetate, after which the aqueous phase formed is decanted, the organic phase is dried over sodium sulphate and decoloured by the addition of animal charcoal. After filtration, the organic phase is evaporated. A crude crystallised residue is recovered and triturated in petroleum ether. The colour partly disappears and, after filtration and drying, 330 g of pale yellow crystals are obtained. Yield 95%.

Melting point: 123.5° C.
Plate chromatography:
support: silica gel 60 F 254 Merck
solvent: ethylacetate/petroleum ether 10/90
development: UV and iodine
Rf: 0.26.

(b) Production of N-methyl-2-tosylamido-5-chlorobenzophenone 308.7 g (0.8 mole) of 2-tosylamido-5-chlorobenzophenone are dissolved in 2 liters of toluene, followed by the addition of a solution of 18.5 g (0.805 atom/g) of sodium in 300 cc of methanol during which the reaction medium is kept at a temperature of 20° C.

Stirring is continued for 15 minutes, followed by the dropwise addition of 201.8 g of methyl sulphate.

After stirring at ambient temperature for 6 hours, the reaction mixture is left standing overnight and then heated for 2 hours at 50° C. and then for 3 hours at 70° C.

1 liter of a 3 N sodium hydroxide solution is added, followed by stirring for 30 minutes. The reaction mixture is decanted, washed 3 times with water until the pH is neutral, dried over sodium sulphate and decoloured with animal charcoal.

After filtration and evaporation to dryness, the thick oil obtained is dissolved in ethanol. On freezing, the resulting solution forms crystals which are recrystallised from ethanol. After filtration and drying, 279.5 g of white crystals are recovered. Yield 87%.

Melting point: 105° C.
Plate chromatography:
support: silica gel 60 F 254 Merck
solvent: ethylacetate/petroleum ether 10/90
development: UV and iodine
Rf: 0.24.

(c) Production of 2-methylamino-5-chlorobenzophenone 1400 cc of 96% sulphuric acid are slowly added to 600 g of ice. After heating to 110° C., 240 g (0.6 mole)

of N-methyl-2-tosylamido-5-chlorobenzophenone are added, the mixture kept for 20 minutes at the temperature of 110° C. and then allowed to cool to ambient temperature.

The free base is introduced into 6 liters of ice water, salted out and crystallised. The crystals are recovered by filtration. These crystals are dissolved in 1.5 liters of ethylacetate, the aqueous phase is decanted and the organic phase is dried over sodium sulphate. After filtration and concentration, 124.5 g of yellow crystals are recovered. Yield 85%.

Melting point: 94° C.
Plate chromatography:
support: silica gel 60 F 254 Merck
solvent: ethylacetate/petroleum ether 10/90
development: UV and iodine
Rf: 0.55.
Remark:

The 2-methylamino-5-chlorobenzophenone may also be prepared by the direct methylation of 2-amino-5-chlorobenzophenone in accordance with the following procedure:

42 cc of methyl sulphate are added to a suspension of 100 g of 2-amino-5-chlorobenzophenone in 500 cc of acetic acid, followed by heating for 2 hours to reflux temperature.

The reaction product is hydrolysed with 2 liters of water and extracted with chloroform.

The organic phase is dried over sodium sulphate.

After evaporation of the organic phase, a slowly crystallising oil is recovered. Recrystallisation from methanol gives 70.8 g of yellow crystals. Yield: 86%.

Melting point: 93.5° C.

(d) Production of N-methyl-(2-benzoyl-4-chloro)-phenyl bromoacetamide

A solution of 2-methylamino-5-chlorobenzophenone in a mixture of 200 cc of benzene and 100 cc of ether is chilled to 0° C., followed by the dropwise addition over a period of 25 minutes of 5.8 cc of bromoacetyl chloride in solution in 40 cc of ether. After standing overnight while stirring at room temperature, the mixture is evaporated to dryness. The oily residue triturated in petroleum ether crystallises rapidly. The crystals are filtered, washed with petroleum ether, dissolved in ethylacetate and decoloured with animal charcoal. After filtration and concentration, precipitation with petroleum ether and filtration, 19.3 g of product are recovered. Yield: 82%.

Melting point: 90° C.
Plate chromatography:
support: silica gel 60 F 254 Merck
solvent: ethylacetate/petroleum ether 25/75
development: UV and iodine
Rf: 0.43.

(e) Production of N-isopropyl-N'-methyl-(2-benzoyl-4-chloro)-glycinanilide hydrochloride 16.98 g of N-methyl-(2-benzoyl-4-chloro)-phenyl bromoacetamide are added in portions to a solution of 34 cc of isopropylamine in 200 cc of acetone. Dissolution is immediate and fairly exothermic.

After addition of the bromine derivative, the mixture is heated for 6 hours at 45° C., left standing overnight and evaporated to dryness under reduced pressure. The residue is taken up in a bicarbonate solution and extracted with ethylacetate. The extract is washed with water, dried over sodium sulphate and decoloured with animal black. After filtration, the product is evaporated to dryness. The residual oil is treated with a saturated solution of hydrochloric acid in ethanol.

Ethyl ether is added to facilitate crystallisation, followed by filtration and drying. 13.18 g of product corresponding to the following formula are recovered:

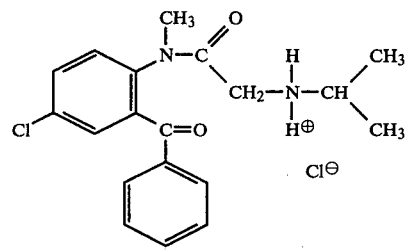

empirical formula: $C_{19}H_{22}Cl_2N_2O_2$
molecular weight: 381.29
white crystals
melting point: 239° C.
plate chromatography:
support: silica gel 60 F 254 Merck
solvent: butanol/acetic acid/water 6/2/2
development: UV and iodine
Rf: 0.53
solubility: 1% in water.

EXAMPLE 2

N-Methyl-N'-1,1-dimethyl-propargyl-(2-benzoyl-4-chloro)-glycinanilide hydrochloride The procedure is as in Example 1, except that 1,1-dimethyl propargylamine is used. The product obtained corresponds to the formula:

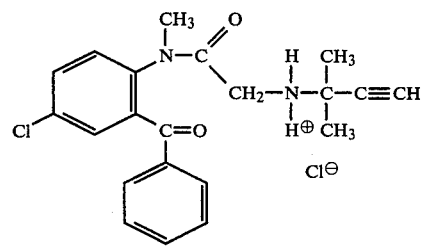

epirical formula: $C_{21}H_{22}Cl_2N_2O_2$
molecular weight: 405.33
white crystals
melting point: 185°–186° C.
plate chromatography:
support: silica gel 60 F 254 Merck
solvent: ethylacetate/petroleum ether 50 50
development: UV and iodine
Rf: 0.37
solubility: 1% in water.

EXAMPLE 3

N,N'-Dimethyl-(2-benzoyl-4-chloro)-glycinanilide hydrochloride

The procedure is as in Example 1, except that methylamine is used. The product obtained corresponds to the formula:

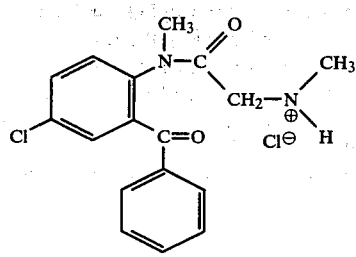

empirical formula: $C_{17}H_{18}Cl_2N_2O_2$
molecular weight: 353.25
white crystals
melting point: 180° C.
plate chromatography:
support: silica gel 60 F 254 Merck
solvent: butanol/acetic acid/water 6/2/2
development: UV and iodine
Rf: 0.37
solubility: 15% in water.

EXAMPLE 4

N,N',N'-Trimethyl-(2-benzoyl-4-chloro)-glycinanilide

The procedure is as in Example 1, except that dimethylamine is used. The product obtained corresponds to the formula:

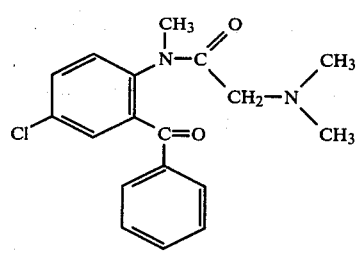

empirical formula: $C_{18}H_{19}ClN_2O_2$
molecular weight: 330.8
white crystals
melting point: 95.5° C.
plate chromatography:
support: silica gel 60 F 254 Merck
solvent: butanol/acetic acid/water 6/2/2
development: UV and iodine
Rf: 0.34
infra-red spectrum: $\nu_{C-H}$ (aromatic) at 3060 cm$^{-1}$; $\nu_{C=O}$ at 1660 cm$^{-1}$; $\nu_{C=C}$ at 1590 cm$^{-1}$
solubilities: insoluble in water; 20% in ethanol at 95° GL and in dimethyl formamide.

EXAMPLE 5

N-Methyl-N'-(2'-methoxyethyl)-(2-benzoyl-4-chloro)-glycinanilide hydrochloride

The procedure is as in Example 1, except that 2-methoxyethylamine is used. The product obtained corresponds to the formula:

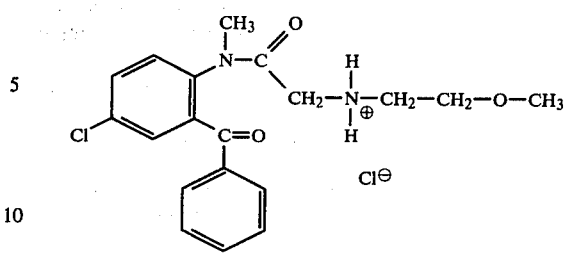

empirical formula: $C_{19}H_{22}Cl_2N_2O_3$
molecular weight: 397.29
white crystals
melting point: 160° C.
plate chromatography:
support: silica gel 60 F 254 Merck
solvent: butanol/acetic acid/water 6/2/2
development: UV and iodine
Rf: 0.52
infra-red spectrum: $\nu_{C=O}$ at 1665 cm$^{-1}$ and $\nu_{C=C}$ at 1595 cm$^{-1}$
solubility: 50% in water.

EXAMPLE 6

N-Methyl-N'-benzyl-(2-benzoyl-4-chloro)-glycinanilide hydrochloride

The procedure is as in Example 1, except that benzylamine is used. The product obtained corresponds to the formula:

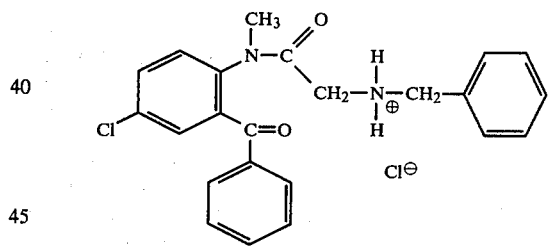

empirical formula: $C_{23}H_{22}Cl_2N_2O_2$
molecular weight: 429.35
beige crystals
melting point: 150° C.
plate chromatography:
support: silica gel 60 F 254 Merck
solvent: ethylacetate
development: UV and iodine
Rf: 0.23
Infra-red spectrum: $\nu_{C=O}$ at 1662 and 1676 cm$^{-1}$
solubility: 2.5% in water.

EXAMPLE 7

N-methyl-N'-allyl-(2-benzoyl-4-chloro)-glycinanilide hydrochloride

The procedure is as in Example 1, except that allylamine is used. The product obtained corresponds to the formula:

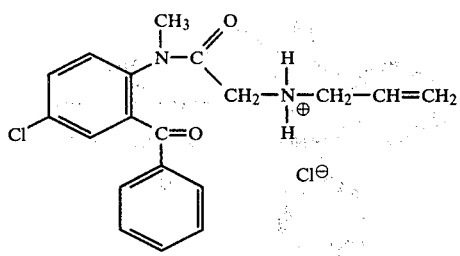

empirical formula: $C_{19}H_{20}Cl_2N_2O_2$
molecular weight: 379.29
white crystals
melting point: 190° C.
plate chromatography:
support: silica gel 60 F 254 Merck
solvent: butanol/acetic acid/water 6/2/2
development: UV and iodine
Rf: 0.56
infra-red spectrum: $\nu_{C=O}$ at 1663 cm$^{-1}$ and $\nu_{C=C}$ at 1598 cm$^{-1}$
solubility: 3% in water.

EXAMPLE 8

N-Methyl-N'-(1',1'-diethyl-propargyl)-(2-benzoyl-4-chloro)-glycinanilide hydrochloride The procedure is as in Example 1, except that 1,1-diethyl-propargylamine is used. The product obtained corresponds to the formula:

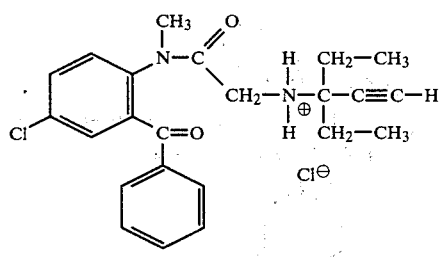

empirical formula: $C_{23}H_{26}Cl_2N_2O_2$
molecular weight: 433.35
white crystals
melting point: 191° C.
plate chromatography:
support: silica gel 60 F 254 Merck
solvent: ethylacetate
development: UV and iodine
Rf: 0.73
infra-red spectrum: $\nu_{\equiv C-H}$ at 3165 cm$^{-1}$; $\nu_{C\equiv C}$ at 2105 cm$^{-1}$; $\nu_{C=O}$ (amide) at 1690 cm$^{-1}$ and $\nu_{C=O}$ (ketone) at 1675 cm$^{-1}$.
solubilities: insoluble in water; 1% in ethanol at 95° GL and in dimethyl formamide.

EXAMPLE 9

N-Methyl-N'-(1'-ethinyl-cyclohexyl)-(2-benzoyl-4-chloro)-glycinanilide hydrochloride The procedure is as in Example 1, except that 1-ethinyl-cyclohexylamine is used. The product obtained corresponds to the formula:

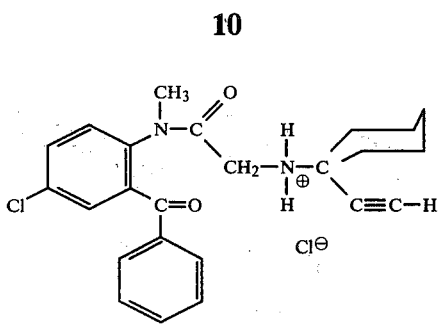

empirical formula: $C_{24}H_{25}Cl_2N_2O_2$
molecular weight: 445.38
white crystals
melting point: 193° C.
plate chromatography:
support: silica gel 60 F 254 Merck
solvent: ethylacetate/petroleum ether 30/70
development: UV and iodine
Rf: 0.31
infrared spectrum: $\nu_{C-H}$ at 3180 cm$^{-1}$; $\nu_{C\equiv C}$ at 2110 cm$^{-1}$; $\nu_{C=O}$ at 1675 cm$^{-1}$.
solubilities: insoluble in water; 3% in ethanol at 95° GL and 2% in dimethyl formamide.

EXAMPLE 10

N-Methyl-N'-cyclopropyl-(2-benzoyl-4-chloro)-glycinanilide hydrochloride

The procedure is as in Example 1, except that cyclopropylamine is used. The product obtained corresponds to the formula:

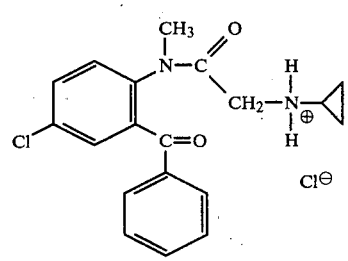

empirical formula: $C_{19}H_{20}Cl_2N_2O_2$
molecular weight: 379.26
white crystals
melting point: 209° C.
plate chromatography
support: silica gel 60 F 254 Merck
solvent: ethylacetate
development: UV and iodine
Rf: 0.27
infrared spectrum: $\nu_{C=O}$ (amide) at 1670 cm$^{-1}$; $\nu_{C=O}$ (ketone) at 1 55 cm$^{-1}$.
solubility: 1.3% in water.

EXAMPLE 11

N-Methyl-N'-cyclohexyl-(2-benzoyl-4-chloro)-glycinanilide hydrochloride

The procedure is as in Example 1, except that cyclohexylamine is used. The products obtained correspond to the formula:

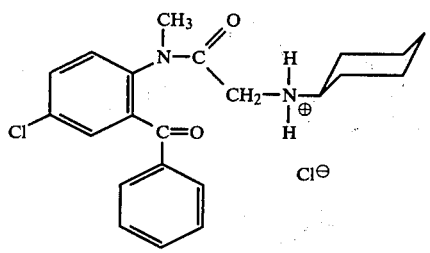

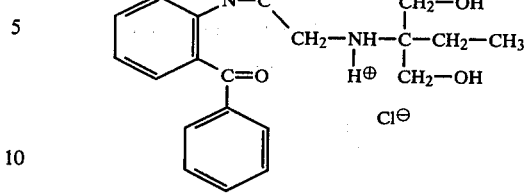

empirical formula: $C_{22}H_{26}Cl_2N_2O_2$
molecular weight: 421.34
white crystals
melting point: 224° C.
plate chromatography:
support: silica gel 60 F 254 Merck
solvent: butanol/acetic acid/water 6/2/2
development: UV and iodine
Rf: 0.61 infrared spectrum: $\nu_{C=O}$ at 1660 cm$^{-1}$ and $\nu_{C=C}$ at 1588 cm$^{-1}$ solubilities: insoluble in water; 3% in ethanol at 95° GL and 1% in dimethyl formamide.

EXAMPLE 12

N-Methyl-N'-(1',1'-dimethyl-2'-hydroxyethyl)-(2-benzoyl-4-chloro)-glycinanilide

The procedure is as in Example 1, except that 2-amino-2-methyl propanol is used. The product obtained corresponds to the formula:

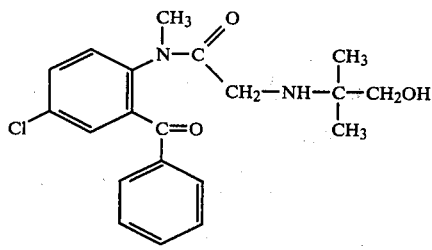

empirical formula: $C_{20}H_{23}Cl\,N_2O_3$
molecular weight: 374.86
lemon-yellow crystals
melting point: 95° C.
plate chromatography:
support: silica gel 60 F 254 Merck
solvent: ethylacetate
development: UV and iodine
Rf: 0.19 infrared spectrum: $\nu_{-OH}$ at 3440 cm$^{-1}$; $\nu_{C=O}$ at 1655 cm$^{-1}$ and $\nu_{C=C}$ at 1598 cm$^{-1}$.

solubilities: insoluble in water; 10% in ethanol at 95° GL and 25% in dimethyl formamide.

EXAMPLE 13

N-Methyl-N'-(1'-ethyl-1'-hydroxymethyl-2'-hydroxyethyl)-(2-benzoyl-4-chloro)-glycinanilide hydrochloride The procedure is as in Example 1, except that 2-amino-2-ethyl-1,3-propane diol is used. The product obtained corresponds to the formula:

empirical formula: $C_{21}H_{26}Cl_2N_2O_4$
molecular weight: 441.36
pale yellow crystals
melting point: 191° C.
plate chromatography:
support: silica gel 60 F 254 Merck
solvent: butanol/acetic acid/water 6/2/2
development: UV and iodine
Rf: 0.47 infra-red spectrum: $\nu_{-OH}$ at 3320 cm$^{-1}$; $\nu_{C=O}$ at 1660 cm$^{-1}$ and $\nu_{C=C}$ at 1596 cm$^{-1}$.

solubility: 50% in water.

EXAMPLE 14

N,N'-dimethyl-N'-(2'-hydroxyethyl)-(2-benzoyl-4-chloro)-glycinanilide

The procedure is as in Example 1, except that N-methylethanolamine is used. The product obtained corresponds to the formula:

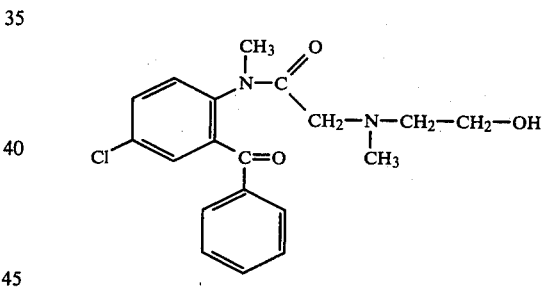

empirical formula: $C_{19}H_{21}Cl\,N_2O_3$
molecular weight: 360.83
white crystals
melting point: 109° C.
plate chromatography:
support: silica gel 60 F 254 Merck
solvent: butanol/acetic acid/water 6/2/2
development: UV and iodine
Rf: 0.47 infrared spectrum: $\nu_{-OH}$ at 3190 cm$^{-1}$; $\nu_{C=O}$ at 1668 cm$^{-1}$ and $\nu_{C=C}$ at 1592 cm$^{-1}$ solubilities: insoluble in water; 20% in ethanol at 95° GL and in dimethyl formamide.

EXAMPLE 15

N-Methyl-N'-ethyl-N'-(2'-hydroxyethyl)-(2-benzoyl-4-chloro)-glycinanilide

The procedure is as in Example 1, except that ethyl-2-aminoethanol is used. The product obtained corresponds to the formula:

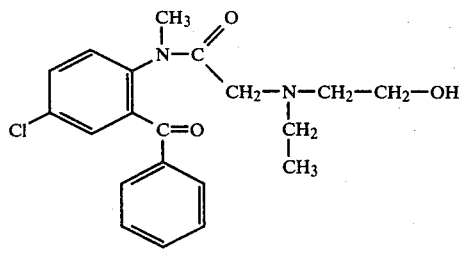

empirical formula: $C_{20}H_{23}ClN_2O_3$
molecular weight: 374.86
white crystals
melting point: 79° C.
plate chromatography:
support: silica gel 60 F 254 Merck
solvent: butanol/acetic acid/water 6/2/2
development: UV and iodine
Rf: 0.35
infrared spectrum: $\nu_{C=O}$ at 1668 cm$^{-1}$; $\nu_{C=C}$ at 1592 cm$^{-1}$.
solubilities: insoluble in water; 10% in ethanol at 95° GL and 30% in dimethyl formamide.

EXAMPLE 16

N-Methyl-N',N'-bis-(2'-hydroxyethyl)-(2-benzoyl-4-chloro)-glycinanilide hydrochloride The procedure is as described in Example 1, except that diethanolamine is used. The product obtained corresponds to the formula:

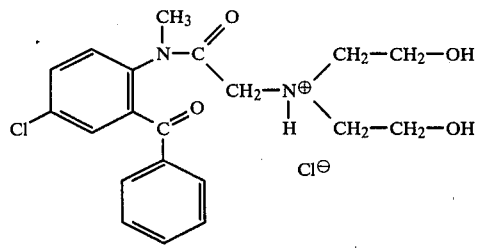

empirical formula: $C_{20}H_{24}Cl_2N_2O_4$
molecular weight: 427.33
white crystals
melting point: 174° C.
plate chromatography:
support: silica gel 60 F 254 Merck
solvent: butanol/acetic acid/water 6/2/2
development: UV and iodine
Rf: 0.35
infrared spectrum: $\nu_{C=O}$ at 1669 cm$^{-1}$ and $\nu_{C=C}$ at 1596 cm$^{-1}$.
solubility: 5% in water.

EXAMPLE 17

N-Methyl-2-piperidino-(2'-benzoyl-4'-chloro)-acetanilide hydrochloride

The procedure is as in Example 1, except that piperidine is used. The product obtained corresponds to the formula:

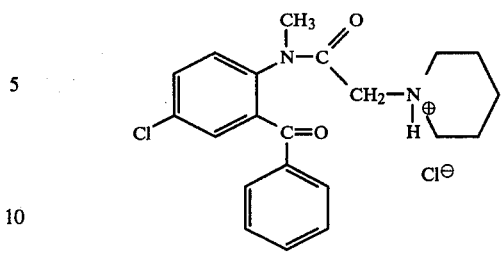

empirical formula: $C_{21}H_{24}Cl_2N_2O_2$
molecular weight: 407.34
white crystals
melting point: 140° C.
plate chromatography:
support: silica gel 60 F 254 Merck
solvent: butanol/acetic acid/water 6/2/2
development: UV and iodine
Rf: 0.55
infrared spectrum: $\nu_{C=O}$ (amide) at 1680 cm$^{-1}$; $\nu_{C=O}$ (ketone) at 1667 cm$^{-1}$; and $\nu_{C=C}$ at 1592 cm$^{-1}$
solubility: 50% in water.

EXAMPLE 18

N-Methyl-2-morpholino-(2'-benzoyl-4'-chloro)-acetanilide hydrochloride

The procedure is as in Example 1, except that morpholine is used. The product obtained corrresponds to the formula:

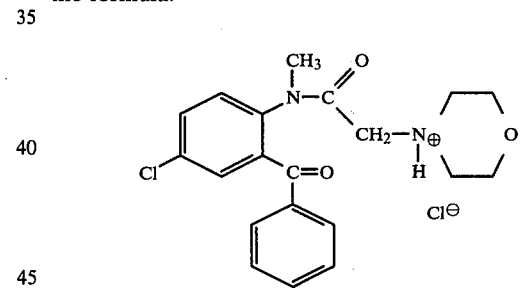

empirical formula: $C_{20}H_{22}Cl_2N_2O_3$
molecular weight: 409.3
white crystals
melting point: 172° C.
plate chromatography:
support: silica gel 60 F 254 Merck
solvent: butanol/acetic acid/water 6/2/2
development: UV and iodine
RF: 0.61
infrared spectrum: $\nu_{C=O}$ at 1663 cm$^{-1}$ and $\nu_{C=C}$ at 1595 cm$^{-1}$
solubility: 10% in water.

EXAMPLE 19

N-Methyl-N'-(2'-methylallyl)-(2-benzoyl-4-chloro)-glycinanilide hydrochloride

The procedure is as in Example 1, except that 2-methylallylamine is used. The product obtained corresponds to the formula:

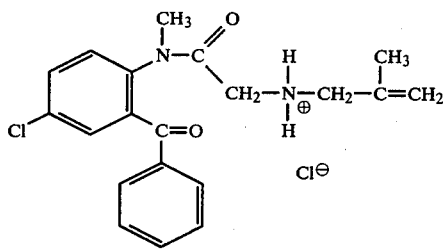

empirical formula: $C_{19}H_{20}Cl_2N_2O_2$
molecular weight: 381.3
white crystals
melting point: 166° C.
plate chromatography:
support: silica gel 60 F 254 Merck
solvent: butanol/acetic acid/water 6/2/2
development: UV and iodine
Rf: 0.54
solubility: 5% in water.

EXAMPLE 20

N,N′-Dimethyl-N′-cyclohexyl-(2-benzoyl-4-chloro)-glycinanilide hydrochloride

The procedure is as in Example 1, except that N-methylcyclohexylamine is used. The product obtained corresponds to the formula:

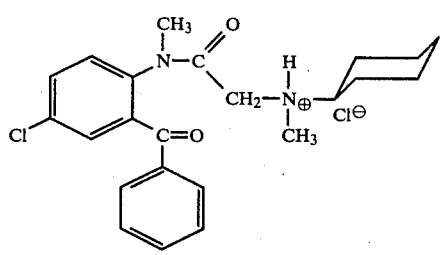

empirical formula: $C_{23}H_{28}Cl_2N_2O_2$
molecular weight: 435.4
white crystals
melting point: 141° C.
plate chromatography:
support: silica gel 60 F 254 Merck
solvent: butanol/acetic acid/water 6/2/2
development: UV and iodine
Rf: 0.43
solubility: 2% in water.

EXAMPLE 21

N-Methyl-N′-isopropyl-N′-cyclohexyl-(2-benzoyl-4-chloro)glycinanilide hydrochloride The procedure is as in Example 1, except that N-isopropylcyclohexylamine is used. The product obtained corresponds to the formula:

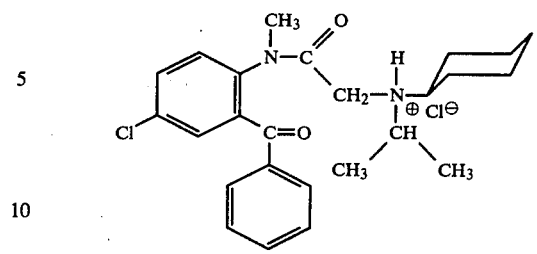

empirical formula: $C_{25}H_{32}Cl_2N_2O_2$
molecular weight: 463.45
yellow crystals
melting point: 145° C.
plate chromatography:
support: silica gel 60 F 254 Merck
solvent: butanol/acetic acid/water 6/2/2
development: UV and iodine
Rf: 0.51
solubility: 5% in water.

EXAMPLE 22

N-Methyl-4′-methyl-2-piperazino-(2-benzoyl-4-chloro)-acetanilide

The procedure is as in Example 1, except that N-methyl piperazine is used. The product obtained corresponds to the formula:

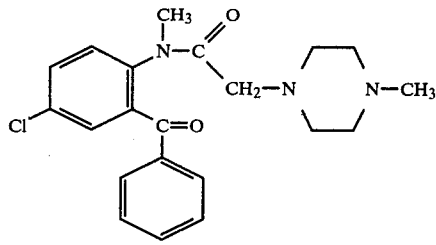

empirical formula: $C_{21}H_{24}Cl\ N_3O_2$
molecular weight: 385.9
white crystals
melting point: 146° C.
plate chromatography:
support: silica gel 60 F 254 Merck
solvent: butanol/acetic acid/water 6/2/2
development: UV and iodine
Rf: 0.20
solubilities: insoluble in water; 5% in ethanol at 95° GL and in dimethyl formamide.

EXAMPLE 23

N-Methyl-2-imidazolyl-(2-benzoyl-4-chloro)-acetanilide

The procedure is as in Example 1, except that imidazole is used. The product obtained corresponds to the formula:

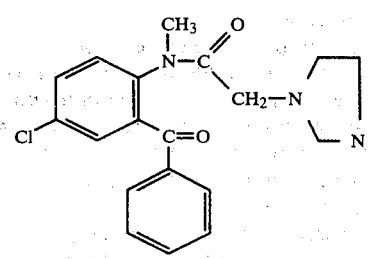

empirical formula: $C_{19}H_{16}Cl\ N_3O_2$
molecular weight: 353.81
white crystals
melting point: 143° C.
plate chromatography:
support: silica gel 60 F 254 Merck
solvent: butanol/acetic acid/water 6/2/2
development: UV and iodine
Rf: 0.39
solubilities: insoluble in water; 10% in ethanol at 95° GL and 20% in dimethyl formamide.

The compounds according to the invention which show remarkable activity on the central nervous system are thus capable of being administered to humans or animals orally or by injection in the form of a free base or even one of its therapeutically accessible salts.

The results of various toxicological and pharmacological tests carried out with the compounds according to the invention are given purely by way of illustration in the following:

(a) Toxicity Test

The compounds according to the invention were subjected to toxicity tests. The toxicity of certain compounds as expressed by the $LD_{50}$ is reported in the following Table. It was tested in batches of 10 mice by oral, intraperitoneal and, in some cases, intravenous administration and was calculated in accordance with Miller and Tainter's method (Proc. Soc. exper. Biol. Med., 1944, 57, 261).

| Compound of Example No. | Results | | |
|---|---|---|---|
| | $DL_{50}$ oral in mg/kg | $DL_{50}$ I.P. in mg/kg | $DL_{50}$ I.V. in mg/kg |
| 2 | >1,000 | 450 | — |
| 5 | 750 | 300 | — |
| 7 | >1,000 | 500 | — |
| 8 | 1,000 | 400 | — |
| 9 | 560 | 200 | — |
| 11 | 1,050 | 305 | 50 |
| 14 | 1,200 | 350 | 55 |
| 15 | 550 | 150 | — |
| 16 | >1,000 | >500 | — |
| 18 | 1,700 | 750 | 103 |
| 19 | 1,500 | 500 | 60 |
| 20 | >1,000 | >500 | — |
| 21 | 1,000 | 500 | — |
| 22 | 1,000 | 500 | — |
| 23 | 1,000 | 500 | — |

(b) Pharmacological Properties

Anti-pentamethylene tetrazole activity

This test is carried out on a group of 10 male mice of the Swiss strain. 15 minutes after the subcutaneous injection of 125 mg/kg of pentamethylene tetrazole, the mice have tonic spasms of which the outcome is fatal. For the test, the compound is administered orally 60 minutes before the injection of pentamethylene tetrazole. The animals are observed for 2 hours after administration of the pentamethylene tetrazole. In some particular cases, the tests were confirmed by intraperitoneal administration. The results are expressed by the effective dose $DE_{50}$ (Goodman et Col.—J. Pharmacol. 108, 1953).

| Compound of Example No. | Results | |
|---|---|---|
| | anti-pentamethylene tetrazole activity $DE_{50}$ - mg/kg P.O. | |
| | P.O. | I.P. |
| 2 | 1.5 | — |
| 5 | 2.6 | — |
| 7 | 1.9 | — |
| 8 | 4.1 | — |
| 9 | 3.9 | — |
| 10 | 0.8 | — |
| 11 | 1.35 | 1.25 |
| 14 | 1.7 | 1.5 |
| 15 | 2.9 | — |
| 16 | 3.4 | — |
| 18 | 3.3 | 1.4 |
| 19 | 1.7 | 1.1 |
| 20 | 1.9 | — |
| 21 | 2.2 | — |
| diazepam | 1 | — |
| chlordiazepoxide | 5 | — |

Prior Art Comparison

As Japanese Pat. No. 148,340 has been cited in co-pending application Ser. No. 916,651, filed June 19, 1978, comparisons between compounds of this closest prior art and the compounds of the invention were undertaken in the form of a controlled study.

The major consideration surrounded the similarity in the compounds, particularly in the substitution at the R position. The study compared ten compounds of the invention, which differed from the Japanese prior art only in that the compounds of the invention are alkylated at the R position while the prior art compounds are all hydrogenated at that position.

The results of the study conclusively establish the pharmacologic activity of the compounds of the invention while demonstrating the total lack of activity of the prior art compounds. This unexpected result dramatizes and clearly points out the great difference between the compounds.

The compounds were tested for anti-pentamethylene tetrazole activity, the test described on p. 29, and the results recorded were as follows:

| R | $R_1$ | $R_2$ | Activity mg/kg antipentetrazol (VO) |
|---|---|---|---|
| H | H | $CH_3$ $\|$ $-C-C\equiv C-H$ $\|$ $CH_3$ | 10 mg (inactive) |
| $CH_3$ | H | $CH_3$ $\|$ $-C-C\equiv C-H$ $\|$ $CH_3$ | 2,3 mg (50% inhibition) |
| H | H | $-CH_2-CH_2-OCH_3$ | 10 mg (inactive) |
| $CH_3$ | H | $-CH_2-CH_2-OCH_3$ | 2,6 mg (50% inhibition) |
| H | H | $-CH_3$ | 10 mg (inactive) |
| $CH_3$ | H | $-CH_3$ | 1,7 mg (50% inhibition) |
| H | $CH_3$ | $-CH_3$ | 10 mg (inactive) |

-continued

| R | R₁ | R₂ | Activity mg/kg antipentetrazol (VO) |
|---|---|---|---|
| CH₃ | CH₃ | —CH₃ | 1,7 mg (50% inhibition) |
| H | H | —C(CH₃)(CH₃) (isopropyl) | 10 mg (inactive) |
| CH₃ | H | —C(CH₃)(CH₃) (isopropyl) | 2,6 mg (50% inhibition) |
| H | H | —CH₂—C₆H₅ | 10 mg (inactive) |
| CH₃ | H | —CH₂—C₆H₅ | 3 mg (50% inhibition) |
| H | H | —CH₂—CH=CH₂ | 10 mg (inactive) |
| CH₃ | H | —CH₂—CH=CH₂ | 1,9 mg (50% inhibition) |
| H | CH₃ | —CH₂—CH₂OH | 10 mg (inactive) |
| CH₃ | CH₃ | —CH₂—CH₂OH | 1,7 mg (50% inhibition) |
| H | H | —CH₂—CH(CH₃)—C₆H₅ | 10 mg (inactive) |
| CH₃ | H | —CH₂—CH(CH₃)—C₆H₅ | 2,9 mg (50% inhibition) |
| H | | =⟨tetrahydropyran-4-ylidene⟩ | 10 mg (inactive) |
| CH₃ | | =⟨tetrahydropyran-4-ylidene⟩ | 3,3 mg (50% inhibition) |

Activity in the Rota-Rod Test

This test is carried out on male Swiss mice. The mouse is placed on a 3 cm diameter wooden rod rotating at 5 revolutions per minute. The mice which succeed in remaining on the rod for at least 3 minutes in successive tests are selected and gathered into groups of 10 for the test of each dose. If the mouse falls off the rod in less than 2 minutes, the tested compound is considered to be effective. The results are expressed by the effective dose DE₅₀ according to N. W. Dunham and T. S. Miva—J. amer. pharm. Ass., 1957, 46, 208.

| Results | |
|---|---|
| Compound of Example No. | Rota Rod DE₅₀ V.O. |
| 11 | 27 |
| 14 | 66 |
| 18 | 60 |
| 19 | 21 |

By virtue of their pharmacological properties, the compounds according to the invention and, more particularly, the compounds of Examples 2, 10, 11, 14, 19 and 20 may be therapeutically used in the treatment of anxiety and neuroses.

These compounds and their addition salts with therapeutically compatible acids may be used as medicaments, for example in the form of pharmaceutical preparations intended for enteral or parenteral administration with, for example, water, lactose, gelatin, starches, magnesium stearate, talcum, vegetable oils, gums, polyalkylene glycols, vaseline, etc.

These preparations may be made up in solid form, for example in the form of tablets, dragees, capsules, etc., or in liquid form, for example in the form of solutions, suspensions or emulsions.

The pharmaceutical preparations in a form suitable for injection are preferred. These preparations may be subjected to conventional pharmaceutical operations, such as sterilisation, and/or may contain adjuvants, for example preservatives, wetting or emulsification stabilisers, buffer compounds, etc.

The doses in which the active compounds and their addition salts with therapeutically compatible acids may be administered may vary within wide limits, according to the condition of the patient. However, a daily dose of about 0.01 mg to 1 mg per kg of body weight is preferred.

The pharmaceutical compositions according to the invention may be used in internal medicine, for example in the treatment of organic pathological states, such as arterial hypertension and coronaritis, accompanied and aggravated by a state of anxiety; in psychosomatic medicine, for example for the treatment of asthma, gastroduodenal ulcers, colonopathy and other functional digestive disorders; and also in phychiatry, for example for the treatment of states of anxious agitation in psychotic subjects.

Naturally the invention is by no means limited to the particular examples mentioned purely by way of illustration. On the contrary, it is entirely possible to imagine a certain number of variants and modifications without departing from the scope of the invention.

We claim:

1. A compound of the formula

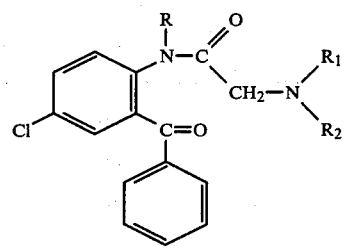

wherein R is methyl,
wherein R₁ is hydrogen, and
wherein R₂ is selected from the group consisting of allyl, diethylpropargyl, ethynylcyclohexyl, cyclopropyl and methylallyl,
or a therapeutically acceptable acid addition salt thereof.

2. A pharmaceutical dosage unit composition consisting essentially of an inert pharmaceutical carrier and an effective anxiolytic amount of a compound according to claim 1, or a therapeutically acceptable acid addition salt thereof.

3. A method for reducing the anxiety of a warm-blooded animal comprising administering to said animal an effective anxiolytic amount of a compound according to claim 1, or a therapeutically acceptable acid addition salt thereof.

4. A compound according to claim 1, which is N-methyl-N'-allyl-(2-benzoyl-4-chloro)-glycinanilide, or a therapeutically acceptable acid addition salt thereof.

5. A compound according to claim 4, which is the hydrochloride of N-methyl-N'-allyl-(2-benzoyl-4-chloro)-glycinanilide.

6. A compound according to claim 1, which is N-methyl-N'-(1',1'-diethyl-propargyl)-(2-benzoyl-4-chloro)-glycinanilide, or a therapeutically acceptable acid addition salt thereof.

7. A compound according to claim 6, which is the hydrochloride of N-methyl-N'-(1',1'-diethyl-propargyl)-(2-benzoyl-4-chloro)-glycinanilide.

8. A compound according to claim 1, which is N-methyl-N'-(1'-ethynyl-cyclohexyl)-(2-benzoyl-4-chloro)-glycinanilide, or a therapeutically acceptable acid addition salt thereof.

9. A compound according to claim 8, which is the hydrochloride of N-methyl-N'-(1'-ethynyl-cyclohexyl)-(2-benzoyl-4-chloro)-glycinanilide.

10. A compound according to claim 1, which is N-methyl-N'-cyclopropyl-(2-benzoyl-4-chloro)-glycinanilide, or a therapeutically acceptable acid addition salt thereof.

11. A compound according to claim 10, which is the hydrochloride of N-methyl-N'-cyclopropyl-(2-benzoyl-4-chloro)-glycinanilide.

12. A compound according to claim 1, which is N-methyl-N'-(2'-methyl-allyl)-(2-benzoyl-4-chloro)-glycinanilide, or a therapeutically acceptable acid addition salt thereof.

13. A compound according to claim 12, which is the hydrochloride of N-methyl-N'-(2'-methyl-allyl)-(2-benzoyl-4-chloro)glycinanilide.

14. The compound N,N'-dimethyl-N'-(2'-hydroxyethyl)-(2-benzoyl-4-chloro)-glycinanilide, or a therapeutically acceptable acid addition salt thereof.

15. The compound according to claim 14, which is N,N'-dimethyl-N'-(2'-hydroxyethyl)-(2-benzoyl-4-chloro)-glycinanilide.

16. A pharmaceutical dosage unit composition consisting essentially of an inert pharmaceutical carrier and an effective anxiolytic amount of the compound according to claim 14, or a therapeutically acceptable acid addition salt thereof.

17. A method for reducing the anxiety of a warm-blooded animal comprising administering to said animal an effective anxiolytic amount of a compound according to claim 14, or a therapeutically acceptable acid addition salt thereof.

* * * * *